(12) United States Patent
Carter et al.

(10) Patent No.: US 9,775,617 B2
(45) Date of Patent: Oct. 3, 2017

(54) CIRCULAR STAPLER INCLUDING BUTTRESS

(71) Applicant: Covidien LP, Mansfield, MA (US)

(72) Inventors: Sally L. Carter, Nashua, NH (US); Richard Stevenson, Colchester, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/682,287

(22) Filed: Apr. 9, 2015

(65) Prior Publication Data

US 2015/0209048 A1    Jul. 30, 2015

Related U.S. Application Data

(62) Division of application No. 13/358,539, filed on Jan. 26, 2012, now Pat. No. 9,010,609.

(51) Int. Cl.
*A61B 17/068* (2006.01)
*A61B 17/115* (2006.01)
(Continued)

(52) U.S. Cl.
CPC ........ *A61B 17/1155* (2013.01); *A61B 17/068* (2013.01); *A61B 17/0686* (2013.01);
(Continued)

(58) Field of Classification Search
CPC ................ A61B 17/068; A61B 17/072; A61B 17/07207; A61B 17/07292; A61B 17/115;
(Continued)

(56) References Cited

U.S. PATENT DOCUMENTS 3,054,406 A    9/1962  Usher
3,079,606 A    3/1963  Bobrov et al.
(Continued)

FOREIGN PATENT DOCUMENTS

CA    2282761 A1    9/1998
CA    2 667 434 A1    5/2008
(Continued)

OTHER PUBLICATIONS

European Office Action corresponding to counterpart Int'l Appln No. EP 12 198 776.2 dated Apr. 7, 2015.
(Continued)

*Primary Examiner* — Scott A. Smith

(57) ABSTRACT

A surgical stapling device for joining tissue portions includes a handle assembly, and a tubular body portion having a staple cartridge assembly containing a plurality of surgical staples in an annular array. The surgical stapling device includes an anvil assembly having a shaft for removably connecting the anvil assembly to the tubular body portion. The anvil assembly and the tubular body portion are juxtaposed with respect to one another along the shaft and are arranged so as to be approximated with respect to one another. The surgical stapling device includes a buttress material supported by the tubular body portion and disposed between the anvil assembly and the staple cartridge assembly. The surgical stapling device includes a suture material that is adapted for engagement with the tubular body portion and the buttress material to secure the buttress material to the tubular body portion.

15 Claims, 15 Drawing Sheets

(51) Int. Cl.
*A61B 17/072* (2006.01)
*A61B 17/00* (2006.01)

(52) U.S. Cl.
CPC .. *A61B 17/07292* (2013.01); *A61B 17/07207* (2013.01); *A61B 2017/00477* (2013.01); *A61B 2017/07214* (2013.01)

(58) Field of Classification Search
CPC ...... A61B 17/1155; A61B 2017/07214; A61B 17/0686
USPC .......... 227/19, 175.1, 176.1, 180.1; 606/139, 606/153, 219
See application file for complete search history.

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,592,354 A * | 6/1986 | Rothfuss ............... A61B 17/115 227/179.1 |
| 4,605,730 A | 8/1986 | Shalaby et al. |
| 4,626,253 A | 12/1986 | Broadnax, Jr. |
| 4,655,221 A | 4/1987 | Devereux |
| 4,665,917 A * | 5/1987 | Clanton ............... A61B 17/115 606/153 |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |

(56) References Cited

U.S. PATENT DOCUMENTS

| | | |
|---|---|---|
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,708,180 B2 * | 5/2010 | Murray ............ A61B 17/00491 227/175.1 |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,138 B2 * | 12/2010 | Dann ............... A61B 17/00234 604/263 |
| 7,846,149 B2 | 12/2010 | Jankowski |
| 7,881,797 B2 * | 2/2011 | Griffin ............... A61N 1/36007 604/264 |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,041 B2 * | 11/2012 | Kostrzewski .... A61B 17/07207 227/175.1 |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 8,870,050 B2 | 10/2014 | Hodgkinson |

(56) References Cited

U.S. PATENT DOCUMENTS

| | | |
|---|---|---|
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | Stopek et al. |
| 9,433,412 B2 | 9/2016 | Bettuchi et al. |
| 9,433,413 B2 | 9/2016 | Stopek |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165559 A1 | 11/2002 | Grant et al. |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0092974 A1* | 5/2004 | Gannoe ............... A61B 17/072 606/153 |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2005/0228446 A1 | 10/2005 | Mooradian et al. |
| 2006/0004407 A1 | 1/2006 | Hiles et al. |
| 2006/0008505 A1 | 1/2006 | Brandon |
| 2006/0085030 A1 | 4/2006 | Bettuchi et al. |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |

(56) References Cited

U.S. PATENT DOCUMENTS

| | | |
|---|---|---|
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0215132 A1 | 9/2011 | Aranyi et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0156289 A1 | 6/2012 | Blaskovich et al. |
| 2012/0187179 A1 | 7/2012 | Gleiman |
| 2012/0197272 A1 | 8/2012 | Oray et al. |
| 2012/0241499 A1 | 9/2012 | Baxter, III et al. |
| 2013/0037596 A1 | 2/2013 | Bear et al. |
| 2013/0105548 A1 | 5/2013 | Hodgkinson et al. |
| 2013/0105553 A1 | 5/2013 | Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0193186 A1 | 8/2013 | Racenet et al. |
| 2013/0193192 A1 | 8/2013 | Casasanta, Jr. et al. |
| 2013/0209659 A1 | 8/2013 | Racenet et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0097224 A1 | 4/2014 | Prior |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |

FOREIGN PATENT DOCUMENTS

| | | |
|---|---|---|
| CN | 101310680 A | 11/2008 |
| CN | 101332110 A | 12/2008 |
| DE | 19924311 A1 | 11/2000 |
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 A1 | 8/2009 |
| EP | 2 090 244 A2 | 8/2009 |
| EP | 2 090 252 A2 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 A1 | 10/2010 |
| EP | 2 258 282 A2 | 12/2010 |
| EP | 2 292 276 A2 | 3/2011 |
| EP | 2 311 386 A2 | 4/2011 |
| EP | 2 436 348 A1 | 4/2012 |
| EP | 2 462 880 A2 | 6/2012 |
| EP | 2 497 431 A1 | 9/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |

(56) References Cited

FOREIGN PATENT DOCUMENTS

| WO | 97/01989 A1 | 1/1997 |
|---|---|---|
| WO | 97/13463 A1 | 4/1997 |
| WO | 98/17180 A1 | 4/1998 |
| WO | 98/38923 A1 | 9/1998 |
| WO | 99/45849 A1 | 9/1999 |
| WO | 03/082126 A1 | 10/2003 |
| WO | 03/088845 A2 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
European Search Report corresponding to EP 05 02 2585.3, completed Jan. 25, 2006 and mailed Feb. 3, 2006; (4 pp).
European Search Report corresponding to EP 06 00 4598, completed Jun. 22, 2006; (2 pp).
European Search Report corresponding to EP 06 01 6962.0, completed Jan. 3, 2007 and mailed Jan. 11, 2007; (10 pp).
International Search Report corresponding to International Application No. PCT/US2005/036740, completed Feb. 20, 2007 and mailed Mar. 23, 2007; (8 pp).
International Search Report corresponding to International Application No. PCT/US2007/022713, completed Apr. 21, 2008 and mailed May 15, 2008; (1 p).
International Search Report corresponding to International Application No. PCT/US2008/002981, completed Jun. 9, 2008 and mailed Jun. 26, 2008; (2 pp).
European Search Report corresponding to EP 08 25 1779, completed Jul. 14, 2008 and mailed Jul. 23, 2008; (5 pp).
European Search Report corresponding to EP 08 25 1989.3, completed Mar. 11, 2010 and mailed Mar. 24, 2010; (6 pp).
European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 2013I; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 13 19 2111.6, completed Feb. 13, 2014 and mailed Feb. 27, 2014; (10 pp).
Extended European Search Report corresponding to EP 13 19 5919.9, completed Feb. 10, 2014 and mailed Mar. 3, 2014; (7 pp).
Extended European Search Report corresponding to EP 08 72 6500.5, completed Feb. 20, 2014 and mailed Mar. 3, 2014; (7 pp).

(56) References Cited

OTHER PUBLICATIONS

Extended European Search Report corresponding to EP 13 19 5019.8, completed Mar. 14, 2014 and mailed Mar. 24, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
Extended European Search Report corresponding to counterpart Int'l Appln. No. EP 12 19 8753.1, dated Feb. 24, 2016.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 mailed Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 mailed Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 mailed Feb. 22, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 mailed May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 mailed Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 mailed Jul. 26, 2016.
Japanese Office Action corresponding to counterpart Int'l Appln. No. JP 2012-268668 mailed Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 mailed Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 mailed Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 mailed Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.

* cited by examiner

CIRCULAR STAPLER INCLUDING BUTTRESS

RELATED APPLICATIONS

The present application is a Divisional Application which claims the benefit of and priority to U.S. patent application Ser. No. 13/358,539, filed Jan. 26, 2012, now U.S. Pat. No. 9,010,609, the content of which is incorporated by reference herein in its entirety.

BACKGROUND

Technical Field

The present disclosure relates to surgical stapling devices and buttress materials for use with said surgical stapling device and, more particularly, to structures and methods for attaching a buttress material to a surgical stapling device for use in anastomosis procedures.

Background of Related Art

Staples have traditionally been used to replace suturing when joining or anastomosing various body structures such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes or buttress materials, are employed by surgeons in combination with linear stapling devices to bridge, repair and/or reinforce tissue defects within a patient, especially those occurring in the abdominal wall, chest wall, diaphragm, and other musculo-aponeurotic areas of the body. Examples of suitable surgical supports are disclosed in U.S. Pat. Nos. 3,054,406, 3,124,136, 4,347,847, 4,655,221, 4,838,884, 5,002,551, and 7,942,890, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw.

While the surgical supports described above are used in conjunction with linear surgical stapling devices, the need exists for annular support structures for use in conjunction with annular or circular surgical stapling devices, for example, an end-to-end anastomosis stapler such as a Model "EEA™" instrument available from United States Surgical, a Division of Tyco Health-Care Group, LP, Norwalk, Conn. and disclosed in U.S. Pat. No. 5,392,979 to Green et al.

One possible side effect of any end-to-end bowel anastomosis is its tendency to undergo stenosis over time, which can decrease the diameter of the lumen over time. Accordingly, the need exists for an annular surgical structure which operates in conjunction with any end-to-end, annular, or circular anastomosis or stapling device and assists in keeping open the lumen of the anastomosed bowel or other tubular organ over time.

A need also exists for an annular support structure which operates in conjunction with any end-to-end, annular or circular stapling device to reduce the trauma suffered by the patient, reduce the instances of leakage, reduce the instances of bleeding, and create a relatively strong bond between adjacent body tissues.

SUMMARY

In one aspect of the present disclosure, a surgical stapling device for joining tissue portions includes a handle assembly and a tubular body portion supported on a distal end of the handle assembly. The tubular body portion has a staple cartridge assembly containing a plurality of surgical staples in an annular array and includes an inner surface and an outer surface. The surgical stapling device further includes an anvil assembly at a distal end of the surgical stapling device having a shaft for removably connecting the anvil assembly to the tubular body portion. The anvil assembly and the tubular body portion are juxtaposed with respect to one another along the shaft and are arranged so as to be approximated with respect to one another. The surgical stapling device further includes a buttress material supported by the tubular body portion and disposed between the anvil assembly and the staple cartridge assembly. The surgical stapling device further includes a suture material that is adapted for engagement with the tubular body portion and the buttress material to secure the buttress material to the tubular body portion. The suture material defines a first end and a second end.

In another aspect of the present disclosure, a distal portion of the tubular body portion includes at least one hole formed through at least one of the inner and outer surfaces and the suture material is adapted to engage the tubular body portion by insertion of at least one of the first and second ends thereof through the at least one hole.

In another aspect of the present disclosure, the first end of the suture material is inserted through a first hole of the tubular body portion and the second end of the suture material is inserted through a second hole of the tubular body portion.

In another aspect of the present disclosure, withdrawal of the suture material from the first and second holes of the tubular body portion is limited by knotting the first and second ends of the suture material together.

In another aspect of the present disclosure, withdrawal of the suture material from the first and second holes of the tubular body portion is limited by sealing the first and second ends of the suture material together.

In another aspect of the present disclosure, withdrawal of at least one of the first and second ends of the suture material from the at least one hole of the tubular body portion is limited by knotting, heat mushrooming, a stop member or a barb.

In another aspect of the present disclosure, a distal portion of the tubular body portion includes at least one attachment member disposed on at least one of the inner and outer surfaces where the suture material is adapted to engage the tubular body portion by engaging the attachment member.

In another aspect of the present disclosure, the at least one hole of the tubular body portion is filled with a gel.

In another aspect of the present disclosure, at least one of the first and second ends of the suture material includes a stop member adapted to limit removal of the at least one of the first and second ends from the at least one hole of the tubular member when inserted therethrough.

In another aspect of the present disclosure, the other of the first and second ends includes a barb.

In another aspect of the present disclosure, the tubular body portion supports a knife blade that is actuatable upon actuation of the handle assembly, the suture material being severable by the knife blade to release the buttress material during firing of the surgical stapling device.

In another aspect of the present disclosure, a surgical stapling device for joining tissue portions includes a handle assembly and a tubular body portion supported on a distal end of the handle assembly. The tubular body portion has a staple cartridge assembly containing a plurality of surgical staples in an annular array. The surgical stapling device further includes an anvil assembly at a distal end of the surgical stapling device having shaft for removably connecting the anvil assembly to the tubular body portion. The anvil assembly and the tubular body portion are juxtaposed with respect to one another along the shaft and are arranged so as to be approximated with respect to one another. The surgical stapling device further includes a buttress material supported by the anvil assembly and disposed between the anvil assembly and the staple cartridge assembly. The surgical stapling device further includes a suture material extending through the buttress material to engage the anvil assembly and adapted to secure the buttress material to the anvil assembly.

In another aspect of the present disclosure, the buttress material includes a flange on an inner portion thereof. The suture material is threaded through the flange and through a lumen extending through the shaft of the anvil assembly to secure the buttress material to the anvil assembly.

In another aspect of the present disclosure, the suture material is annularly stitched through the buttress material about the shaft of the anvil assembly and is transitionable between a first configuration and a second configuration, the second configuration defining a smaller diameter than the first configuration for securing the buttress material to the shaft of the anvil assembly.

In another aspect of the present disclosure, a method of using a buttress material with a surgical stapling device includes the steps of positioning the buttress material at least partially between an anvil assembly and a cartridge assembly of the surgical stapling device, securing the buttress material to the surgical stapling device by engaging a suture material with the buttress material and engaging the suture material with the surgical stapling device, receiving body tissue between the anvil assembly and the cartridge assembly, grasping the body tissue between the anvil assembly and the cartridge assembly, firing the surgical stapling device to drive a plurality of staples from the cartridge assembly through the buttress material and the body tissue, and releasing the suture material from the surgical stapling device to release the buttress material from the surgical stapling device.

In another aspect of the present disclosure, the step of securing the buttress material to the surgical stapling device includes the step of inserting at least one end of the suture material through at least one hole of one of the anvil assembly and the tubular body portion.

In another aspect of the present disclosure, the step of securing the buttress material to the surgical stapling device includes the step of attaching first and second ends of the suture material together after the first and second ends of the suture material have been inserted through the at least one hole.

In another aspect of the present disclosure, the step of releasing the suture material includes the step of severing the suture material with a knife blade disposed in the tubular body portion and movable relative to the tubular body portion.

In another aspect of the present disclosure, the step of securing the buttress material to the surgical stapling device includes the step of removably attaching the suture material to an attachment member of the surgical stapling device.

In another aspect of the present disclosure, the step of releasing the suture material includes the step of releasing the suture material from the attachment member of the surgical stapling device.

Any of the above aspects of the present disclosure described may be combined with any other aspect of the present disclosure without departing from the scope of the present disclosure.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Figure 1:
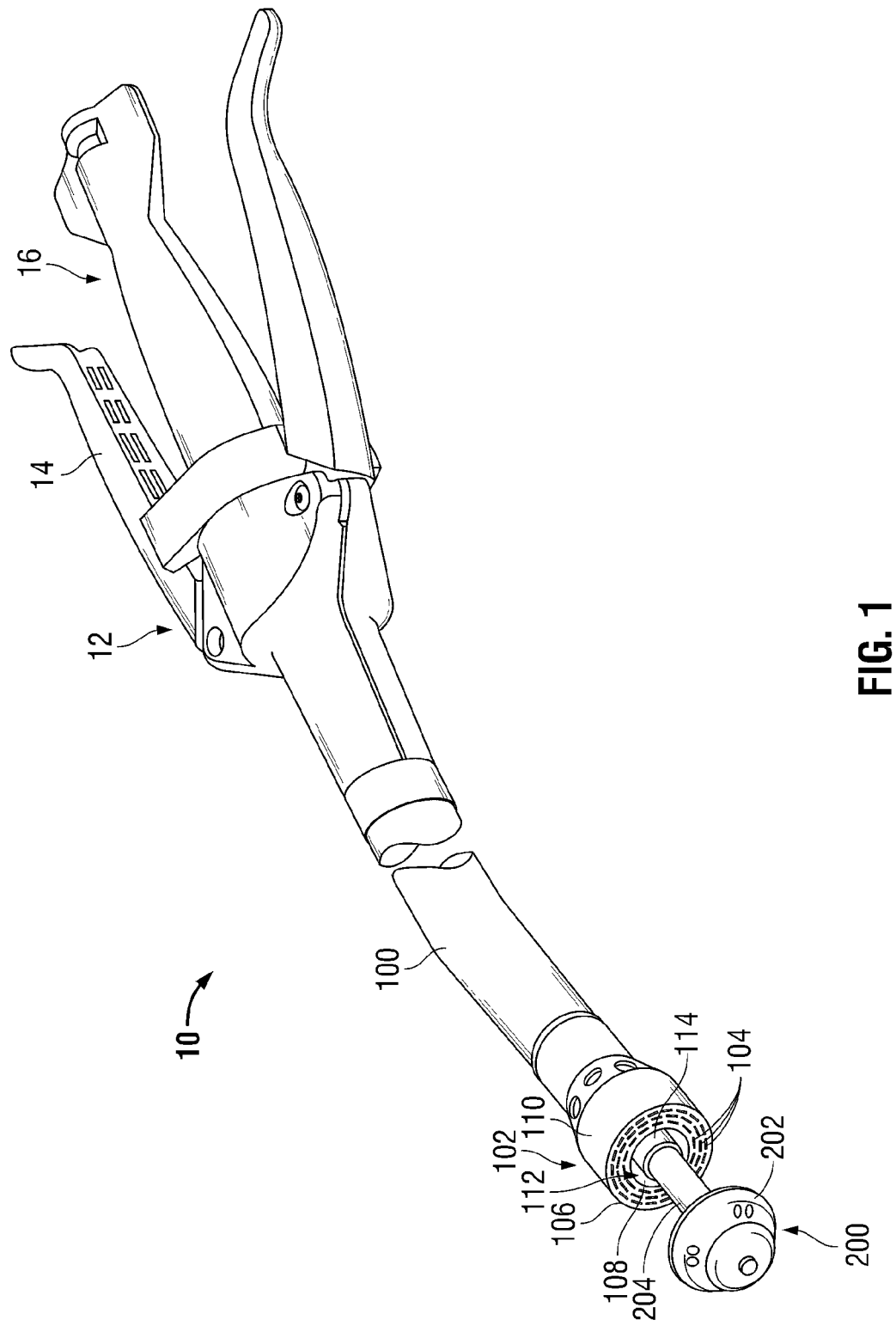
FIG. 1 is a perspective view of an exemplary annular surgical stapling device according to the present disclosure.

Embodiments of the presently disclosed annular surgical stapling device will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Figure 3:
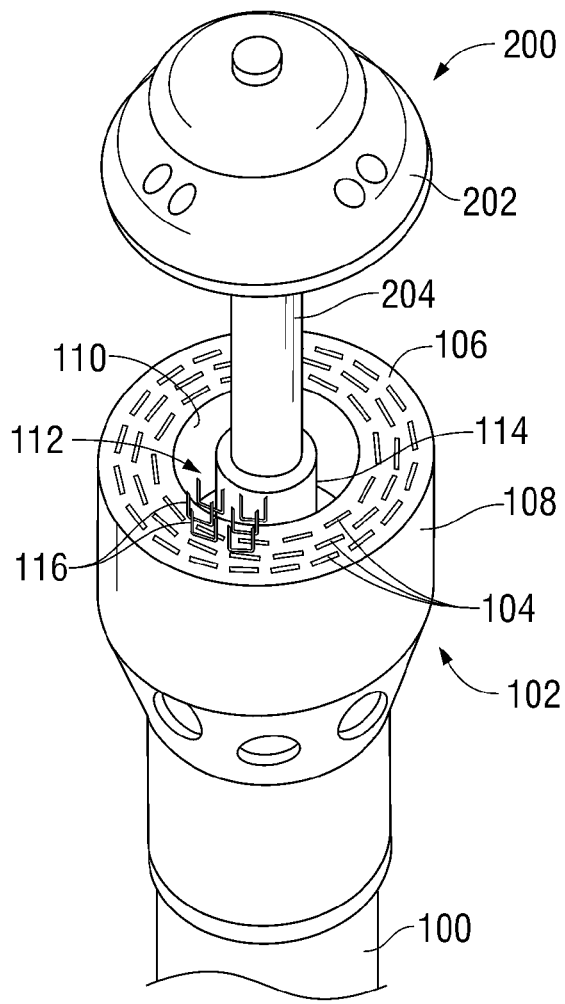
FIG. 3 is an enlarged perspective view of an anvil assembly and a tubular body portion of the annular surgical stapling device of FIG. 1.

Referring initially to FIGS. 1 and 3, an annular surgical stapling device for use with a buttress material is disclosed herein and is generally designated as 10. Surgical stapling device 10 includes a handle assembly 12 having at least one pivotable actuating handle member 14, and an advancing member 16. Extending from handle member 12, there is provided a tubular body portion 100 which may be constructed so as to have a curved shape along its length. Body portion 100 terminates in a staple cartridge assembly 102 defining an inner surface 108 and an outer surface 110. Staple cartridge assembly 102 includes at least one annular array of staple receiving slots 104 disposed at a distal end and a staple 116 disposed in each of staple receiving slots 104. For example, staple cartridge assembly 102 may include one, two, or more than two annular arrays of staple receiving slots 104. Staple receiving slots 104 extend through a tissue contacting surface 106 of the distal end of the staple cartridge assembly 102.

Staple cartridge assembly 102 may be fixedly connected to the distal end of tubular body portion 100 or may be configured to concentrically fit within the distal end of tubular body portion 100. Typically, staple cartridge assembly 102 includes a staple pusher (not shown) including a proximal portion having a generally frusto-conical shape and a distal portion defining two concentric rings of peripherally spaced fingers (not shown), each one of which is received within one of the respective staple receiving slots 104.

Typically, a knife 118 (see FIG. 8), substantially in the form of an open cup with the rim thereof defining a knife edge, is disposed within staple cartridge assembly 102 and mounted to a distal surface of a staple pusher (not shown). The knife edge is disposed radially inward of the pair of annular arrays of staples. Accordingly, in use, as the staple pusher is advanced, the knife 118 is also advanced axially outward.

Positioned distally of staple cartridge assembly 102 there is provided an anvil assembly 200 including an anvil member 202 and a shaft 204 operatively associated therewith for removably connecting anvil assembly 200 to a distal end portion of stapling device 10. Inner wall 108 forms an opening 112 in the distal end of staple cartridge assembly 102 and tubular body portion 100 includes a central shaft 114 extending through opening 112 for engagement with shaft 204 of anvil assembly 200.

Reference may be made to U.S. Pat. No. 5,915,616 to Viola et al., the entire contents of which are incorporated herein by reference, for a detailed discussion of the construction and operation of annular stapling device 10.

Figure 2:
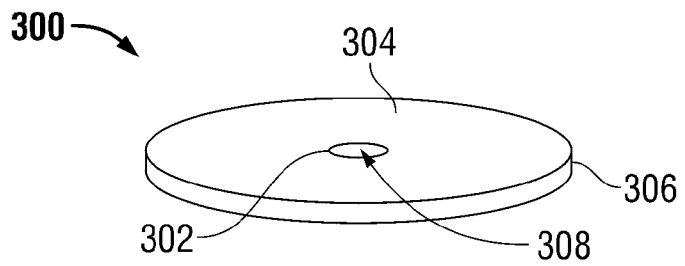
FIG. 2 is a perspective view of a buttress material in accordance with an embodiment of the present disclosure, for use with the annular surgical stapling device of FIG. 1.

Referring now to FIG. 2, a buttress material 300 is generally annular in shape and includes an inner portion 302, a middle portion 304, and an outer portion 306. A substantially centrally located aperture 308, defined by the inner circumference of inner portion 302 is formed through buttress material 300. Buttress material 300 may be any shape sufficient to provide support for anastomosis of tissue after surgical stapling device 10 has been fired including, for example, a square, a circle, an oval, a triangle or any other polygonal or other shape.

Figure 4B:
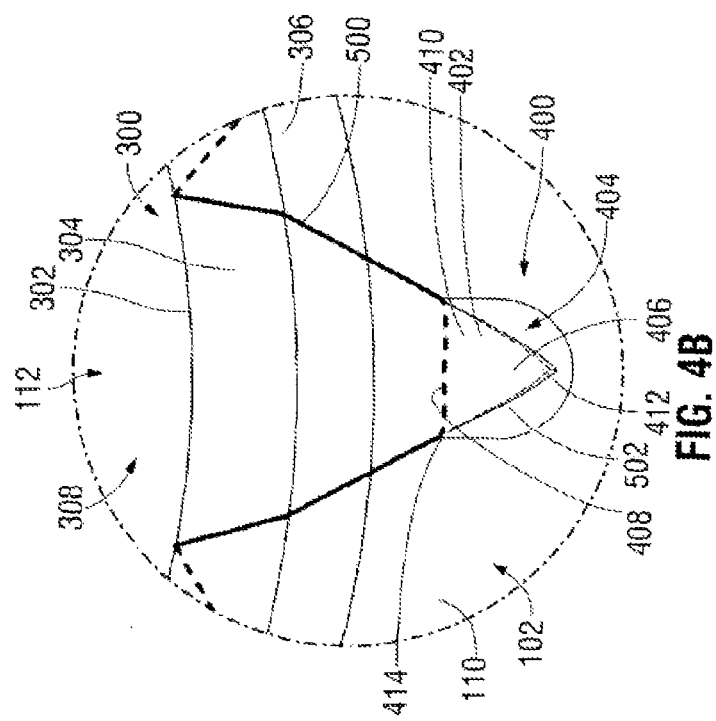
FIG. 4B is a detail view of a portion of the tubular body portion of FIG. 4A, illustrating one of the attachment points.
Figure 4A:
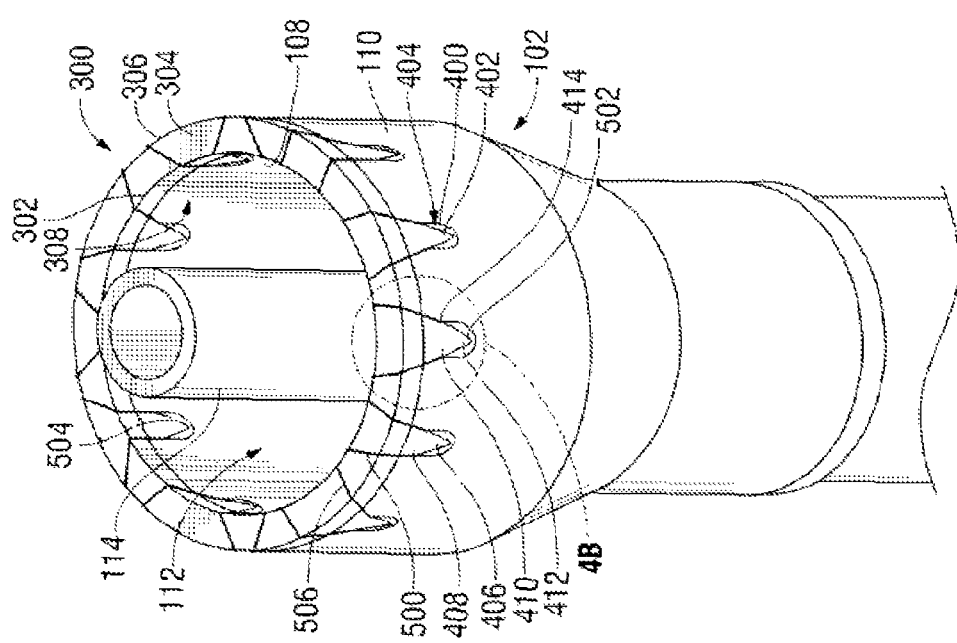
FIG. 4A is an enlarged perspective view of a tubular body portion of the annular surgical stapling device of FIG. 1, illustrating attachment points according to an embodiment of the present disclosure.
Figure 4C:
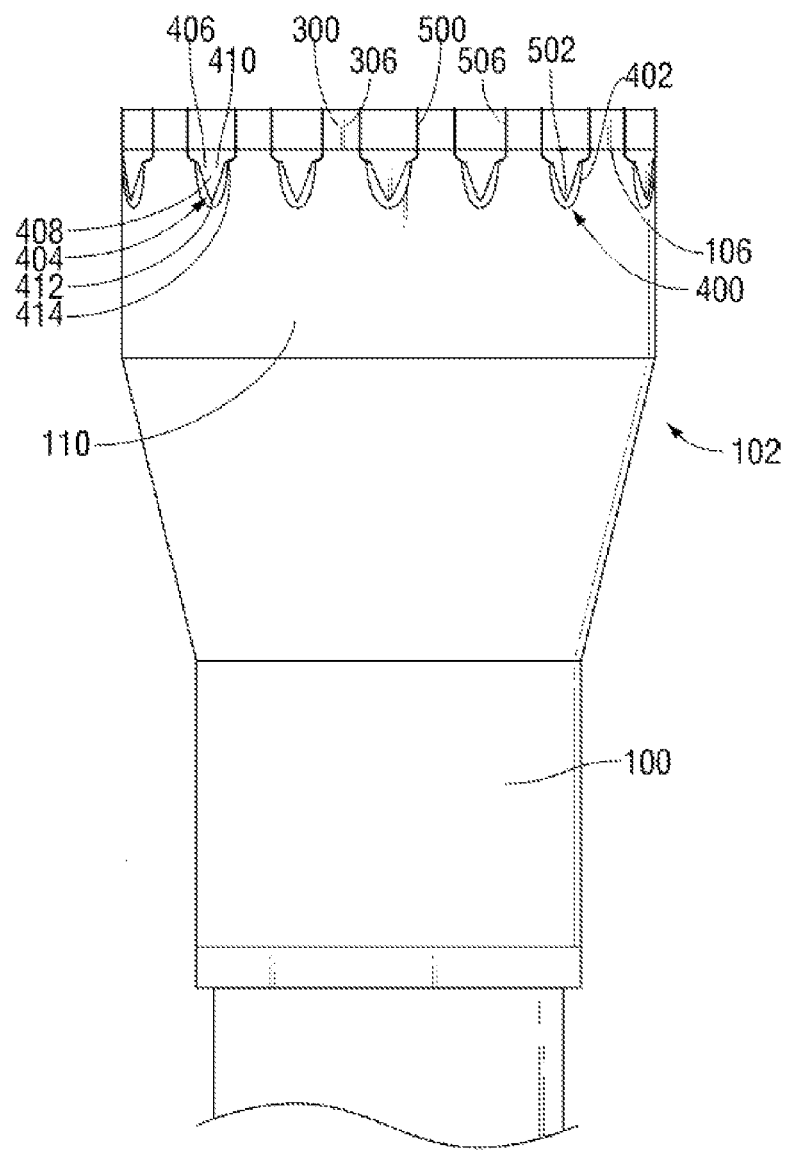
FIG. 4C is a side, elevational view of the tubular body portion of FIG. 4A.

As illustrated in FIGS. 4A-4C, buttress material 300 is sized such that when buttress material 300 is positioned over tissue contacting surface 106, inner portion 302 and outer portion 306 of buttress material 300 are substantially axially aligned with inner surface 108 and outer surface 110 of staple cartridge assembly 102, respectively. Aperture 308 of buttress material 300 is sized to at least receive shaft 204 of anvil assembly 200 and central shaft 114 of tubular body portion 100 therethrough and, in certain embodiments, may be substantially the same size as opening 112. It is also contemplated that buttress material 300 may extend radially beyond inner and outer surfaces 108, 110, respectively.

Each portion 302, 304, and 306 of buttress material 300 may be fabricated from surgical grade, biocompatible, non-absorbable material (i.e. permanent) or absorbable material (i.e. non-permanent) mesh or material desirably impregnated with an adhesive, sealant and/or other medicament. It is also contemplated that each portion may be a composite of both a non-absorbable and an absorbable material. Suitable materials for the fabrication of buttress material 300 and suitable adhesives, sealants, and/or medicaments for impregnation in or application to buttress material 300 may be found, for example, in U.S. Pat. No. 7,942,890, referenced above.

Buttress material 300 may be secured to staple cartridge assembly 102 through the use of one or more sutures 500, as illustrated in FIGS. 4A-4C, 5A-5D, 6A-6C and 7A-7C. Generally, each suture 500 includes a leading end 502, a trailing end 504 and a body portion 506 extending between the leading and trailing ends 502, 504, as will be described in the embodiments to follow.

Similar to buttress material 300, sutures 500 may be fabricated from surgical grade, biocompatible, non-absorbable material (i.e. permanent) or absorbable material (i.e. non-permanent) or material desirably impregnated with an adhesive, sealant and/or other medicament. It is also contemplated that sutures 500 may be a composite of both a non-absorbable and an absorbable material. Suitable materials are described above with reference to buttress material 300.

In one embodiment, with reference to FIGS. 4A-4C, cartridge assembly 102 includes a plurality of attachment points 400 disposed on or about inner and outer surfaces 108, 110 for attaching or securing a length of suture 500 thereto. Although attachment points 400 are illustrated as cleats 402 in FIGS. 4A-4C, attachment points 400 may also be in the form of buttons, knobs, holes or other similar mechanisms for receiving and securing suture 500 thereto.

Each cleat 402 includes an opening or depression 404 extending into the inner or outer surface 108, 110 of the staple cartridge assembly 102 defining a substantially arcuate or U-shape profile having a substantially linear distal edge 408. Each cleat 402 includes a tab 406 extending from the distal edge 408 into opening 404 and includes a base portion 410 and a tip portion 412. Tip portion 412 is dimensioned to allow body portion 506 of suture 500 to be inserted between tip portion 412 and opening 404 of cleat 402. Base portion 410 forms wedge points 414 with opening 404 for securing body portion 506 of suture 500 to cleat 402. It is contemplated that opening 404 may define other shapes such as, for example squares, rectangles, triangles, or other shapes suitable for receiving and securing a portion of suture 500 therein. Although illustrated as being substantially triangular in shape, tab 406 may alternatively include a rounded tip portion 412, a squared off tip portion 412, or another suitably shaped tip portion 412 so long as the portion of suture 500 is insertable between tip portion 412 and opening 404 and securable by wedge points 414.

As illustrated in FIGS. 4A-4C, cleats 402 are disposed on both inner and outer surfaces 108, 110 of staple cartridge assembly 102 such that one or more lengths of suture 500 can be alternately secured to cleats 402 on the inner surface 108 and the outer surface 110 of staple cartridge assembly 102 to secure buttress material 300 to the tissue contacting surface 106 of staple cartridge assembly 102. For example, a single suture 500 may be wound through a first of cleats 402 on the outer surface 110 of staple cartridge assembly 102 and then drawn distally over buttress material 300 to engage buttress material 300 before being wound through a second of cleats 402 on the inner surface 108 of staple cartridge assembly 102, thereby securing buttress material 300 to tissue contacting surface 106 of staple cartridge assembly 102. Each pair of inner and outer cleats 402 may receive a separate suture 500 or a single suture 500 may be wound continuously through each of cleats 402. Alternatively a single suture 500 may be secured to any number of cleats 402 where, for example, one, two or more sutures 500 may be included.

The first cleat 402 on the inner surface 108 of staple cartridge assembly 102 and the second cleat 402 on the outer surface 110 of staple cartridge assembly 102 may be substantially radially aligned with respect to one another or may be radially offset with respect to one another (See FIGS. 4A-4C), for example, to facilitate weaving suture 500 between more than one pair of cleats 402.

It is contemplated that attachment points 400 may alternatively be holes (not shown) where, for example, one or more sutures 500 are inserted through one or more holes on outer surface 110, are being wound over buttress material 300 in a similar manner as described above for cleats 402, and are further inserted through holes (not shown) on inner surface 120. Suture 500 may be wound back and forth over buttress material 300 between the holes (not shown) in outer and inner surfaces 110, 120 to secure buttress material 300 to staple cartridge assembly 102.

Sutures 500 are configured to break free from staple cartridge assembly 102, or to be severed, upon firing of the annular surgical stapling device 10 to allow buttress material 300 to separate from tissue contacting surface 106 of staple cartridge assembly 102 after anastomosis has occurred. For, example, suture 500 may be configured to break free upon release of anastomized tissue from between the staple cartridge assembly 102 and the anvil assembly 200 or after the firing procedure is complete as the surgical stapling device 10 is withdrawn from the surgical site.

Suture 500 may also include weakened portions or sections along body portion 506 or at leading and trailing ends 502, 504 at which suture 500 may break or sever upon application of force along its length.

Suture 500 may also or alternatively, as mentioned above, be configured to be cut or severed by knife 118 as the knife 118 is actuated during the firing process where, for example, the portion of suture 500 disposed radially inward of inner surface 108 may be severed by knife 118 during firing of surgical stapling device 10. The surgeon may also manipulate suture 500 to release suture 500 from staple cartridge assembly 102.

Figure 5A:
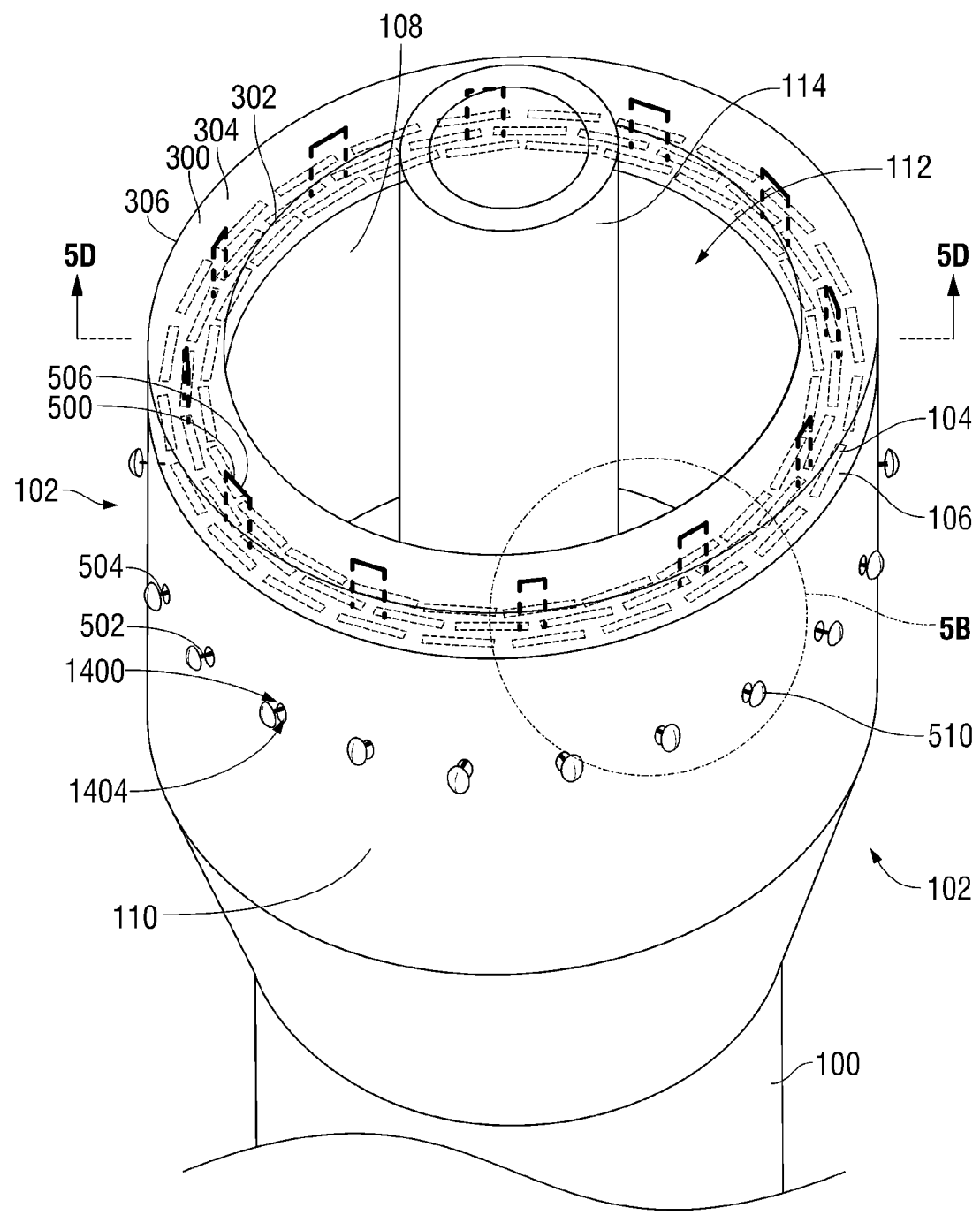
FIG. 5A is an enlarged perspective view of a tubular body portion of the annular surgical stapling device of FIG. 1, illustrating attachment points according to another embodiment of the present disclosure.
Figure 5C:
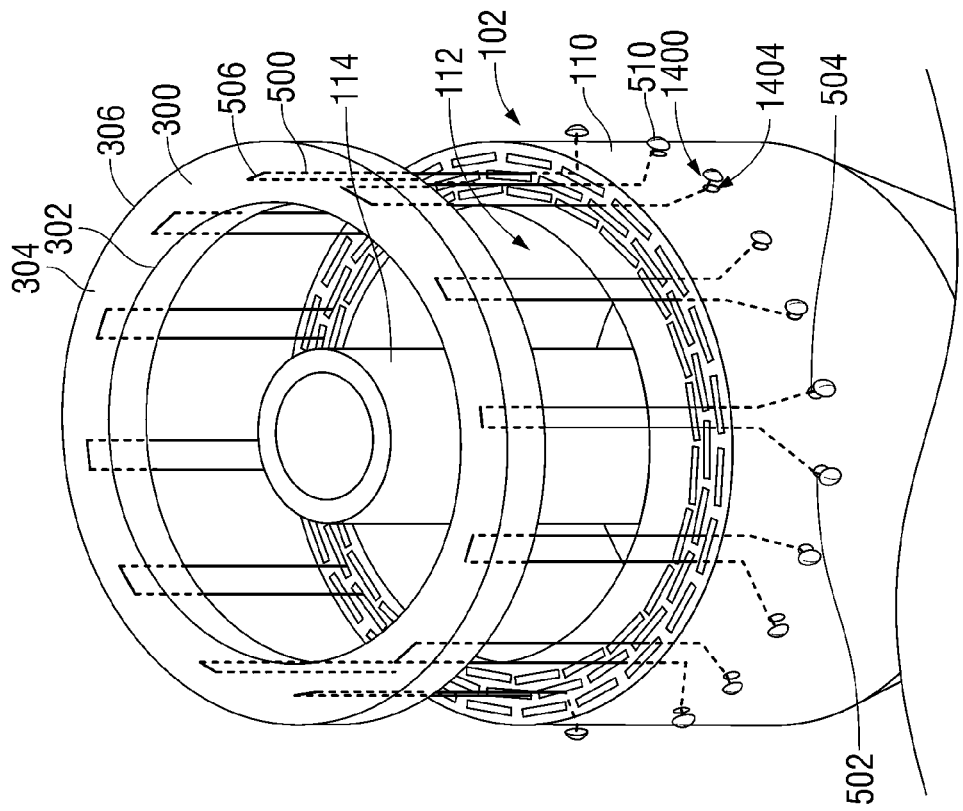
FIG. 5C is a perspective view, with parts separated, of the tubular body portion of FIG. 5A.
Figure 5B:
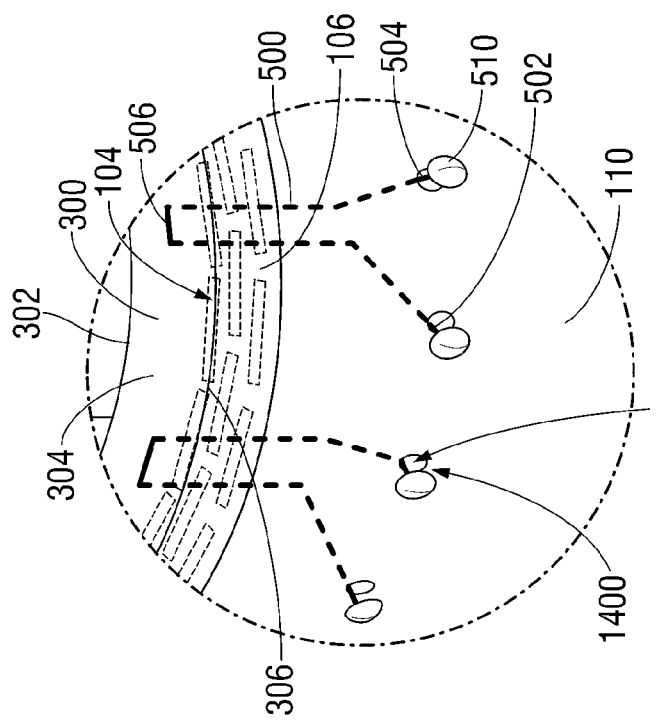
FIG. 5B is a detail view of a portion of the tubular body portion of FIG. 5A, illustrating the attachment points.
Figure 5D:
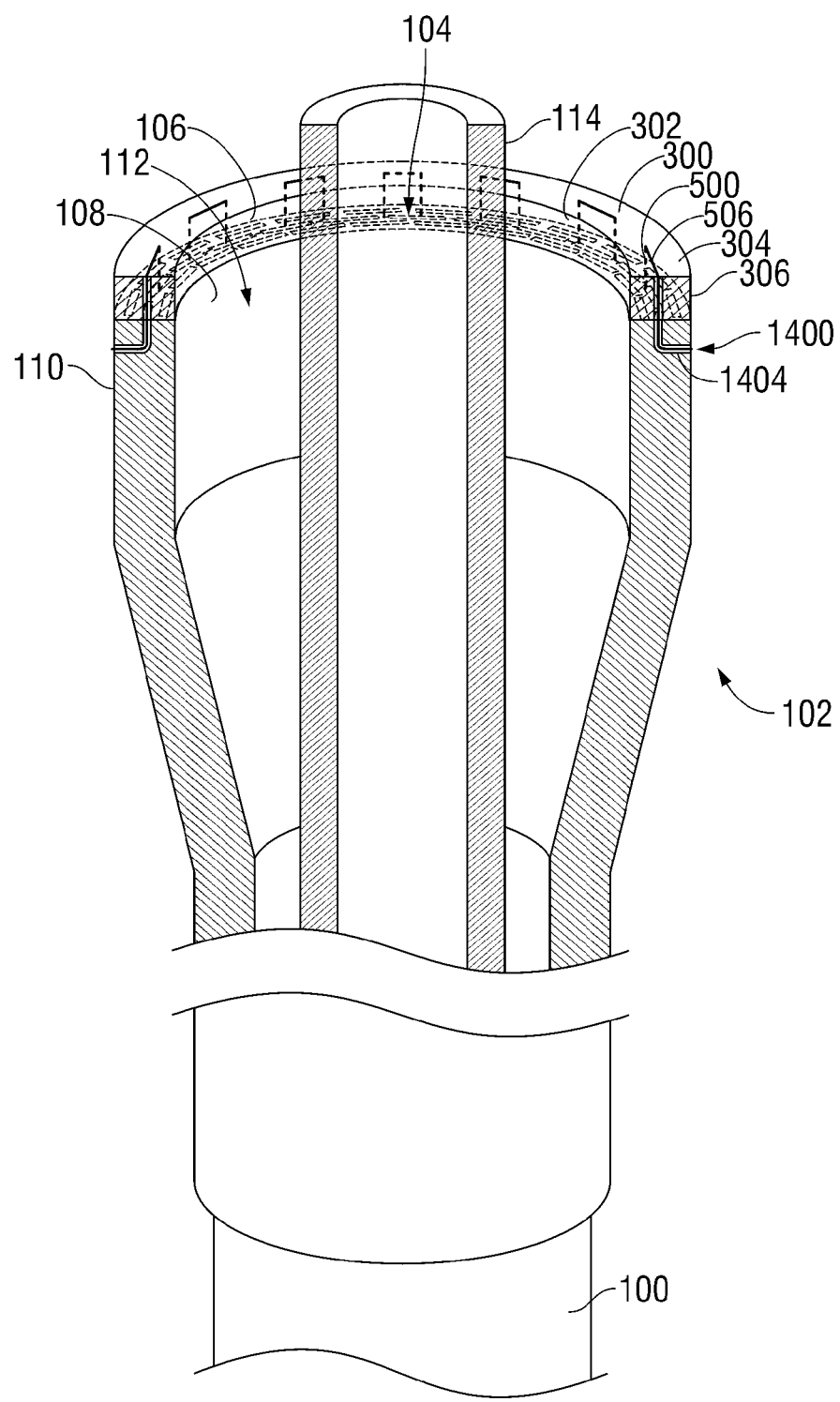
FIG. 5D is a perspective, longitudinal, cross-sectional view of the tubular body portion of FIG. 5A, as taken through 5D-5D of FIG. 5A, illustrating the suture extending through the openings.

In another embodiment, as illustrated in FIGS. 5A-5D and 6A-6C attachment points 1400 include openings 1404 extending through outer surface 110 of staple cartridge assembly 102. In this embodiment, sutures 500 are inserted through mesh 300 and through the tissue contacting surface 106 of staple cartridge assembly 102. For example, leading and trailing ends 502, 504 of sutures 500 are inserted through staple receiving slots 104. Sutures 500 are inserted through staple cartridge assembly 102 and through openings 1404 in outer surface 110 of staple cartridge assembly 102. Each of leading and trailing ends 502, 504 of suture 500 may extend through a different opening 1404 (See FIGS. 5B and 6B) or both of leading and trailing ends 502, 504 may extend through the same opening 1404. As illustrated in FIG. 5D, sutures 500 are drawn through openings 1404 until body portion 506 engages buttress material 300 to secure buttress material 300 to tissue contacting surface 106 of staple cartridge assembly 102.

As illustrated in FIGS. 5A-5C, each of leading and trailing ends 502, 504 of sutures 500 are secured in place through the use of knotting, heat mushrooming, buttons, stop members or other similar methods which will limit or prevent leading and trailing ends 502, 504 of sutures 500 from being withdrawn through openings 1404.

Figure 6A:
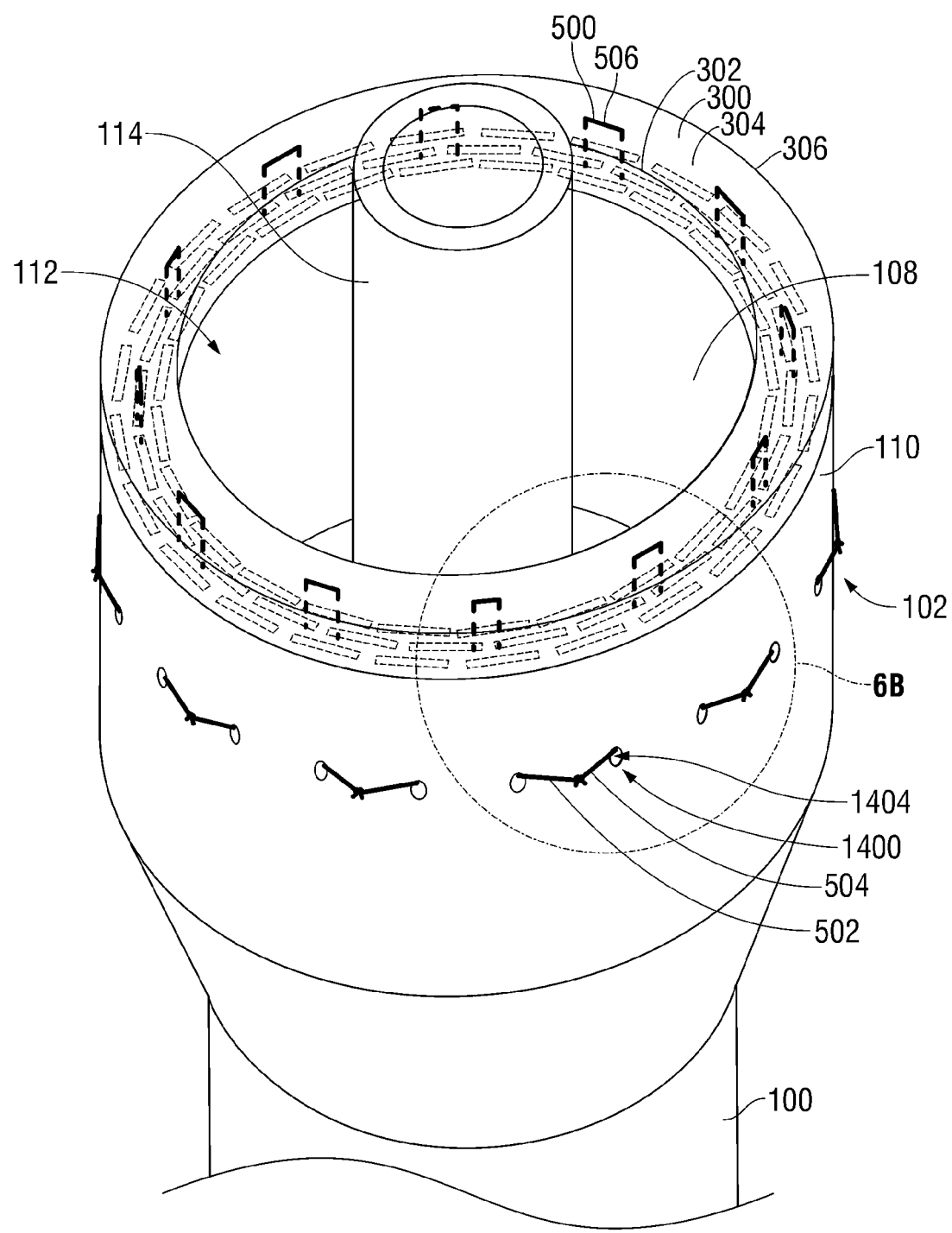
FIG. 6A is an enlarged perspective view of a tubular body portion of the annular surgical stapling device of FIG. 1, illustrating attachment points according to another embodiment of the present disclosure.
Figure 6C:
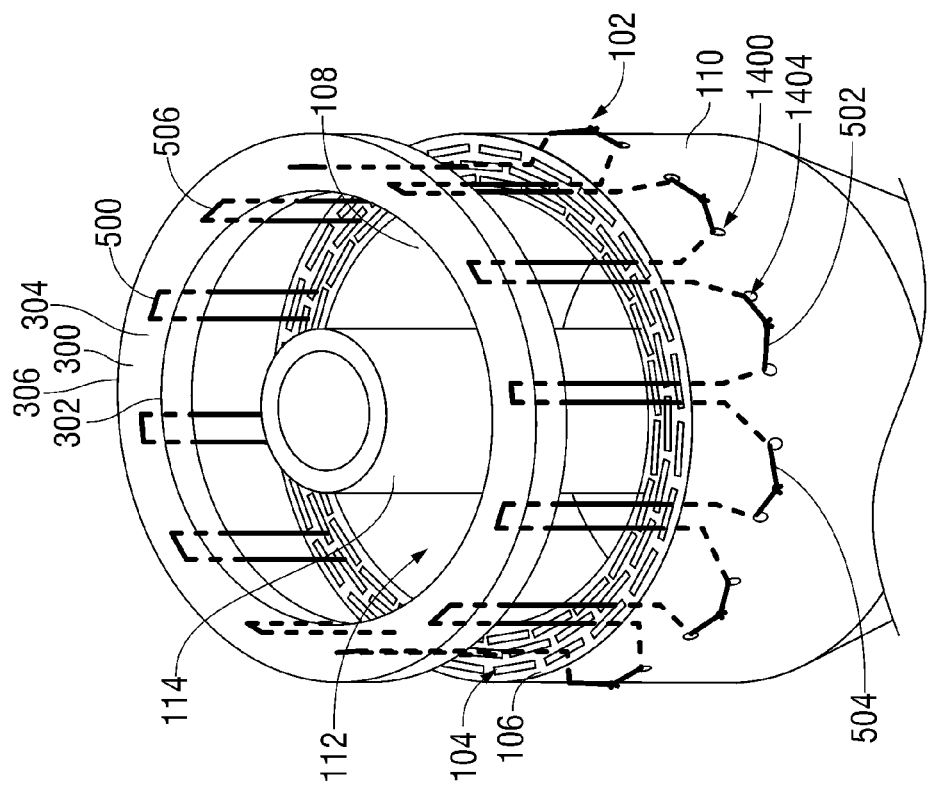
FIG. 6C is a perspective view, with parts separated, of the tubular body portion of FIG. 6A.
Figure 6B:
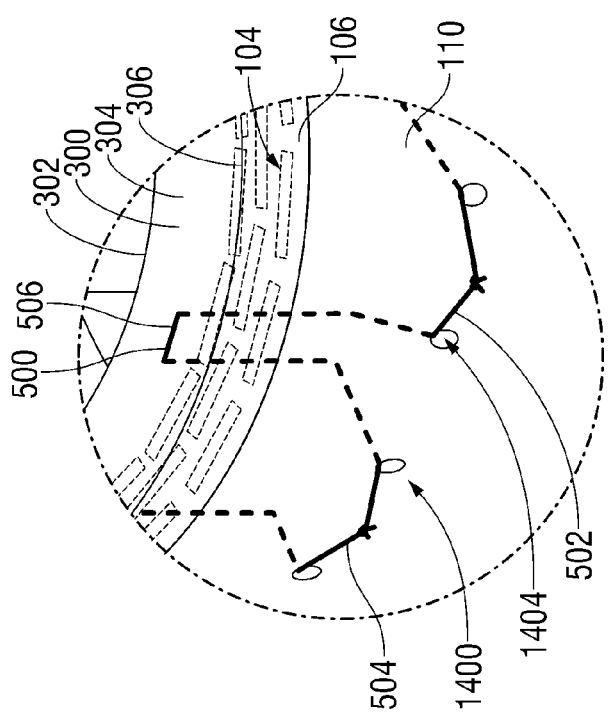
FIG. 6B is a detail view of a portion of the tubular body portion of FIG. 6A, illustrating the attachment points.

Alternatively, as illustrated in FIGS. 6A-6C, leading and trailing ends 502, 504 of sutures 500 may be joined together through knotting, fusing, or other similar methods of combining or attaching leading and trailing ends 502, 504 of sutures 500 together to limit or prevent leading and trailing ends 502, 504 of sutures 500 from being withdrawn through openings 1404. It is contemplated that openings 1404 may alternatively or additionally extend through inner surface 108 of staple cartridge assembly 102.

Sutures 500 are configured to break free or be severed from staple cartridge assembly 102 upon firing of the annular surgical stapling device 10 to allow buttress material 300 to separate from tissue contacting surface 106 of staple cartridge assembly 102 after anastomosis has occurred. For example, as a staple 116 is driven through one of the staple receiving slots 104 through which a suture 500 extends, the staple 116 may pierce, puncture or otherwise tear the suture 500 to release buttress material 300 from staple cartridge assembly 102. The suture 500 may also or alternatively be configured to break upon release of anastomized tissue from between the staple cartridge assembly 102 and the anvil assembly 200 or after the firing procedure is complete as the surgical stapling device 10 is withdrawn from the surgical site. For example, the suture 500 may include weakened portions or sections along body portion 506 or at leading and trailing ends 502, 504 of suture 500 at which suture 500 may break or sever upon application of force along its length. The surgeon may also manipulate the suture 500 to release suture 500 from staple cartridge assembly 102. The knife 118 may also be used to sever a portion of suture 500 extending through the openings 1404 in inner surface 108 of staple cartridge assembly 102 during firing of surgical stapling device 10.

Figure 7A:
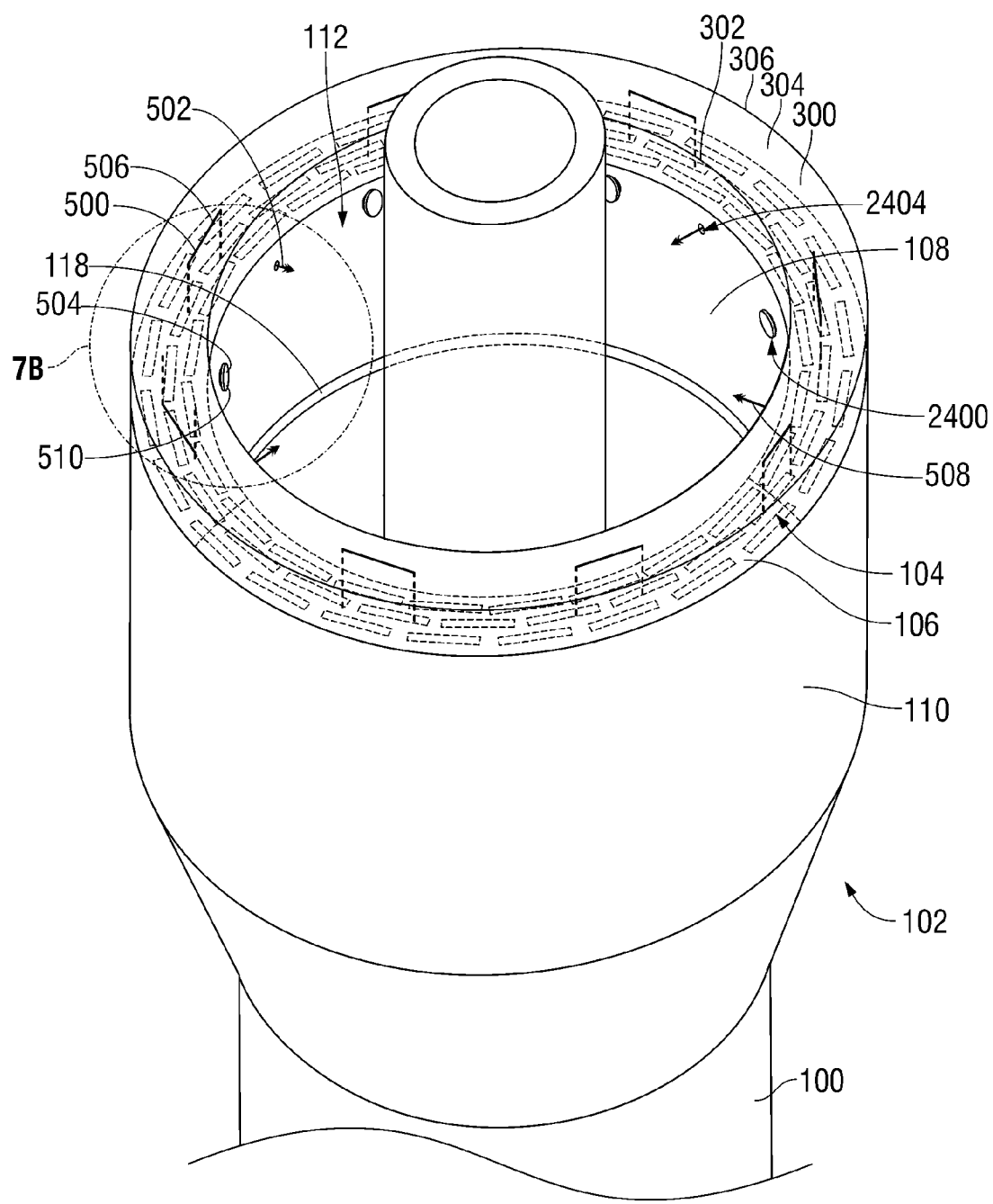
FIG. 7A is an enlarged perspective view of a tubular body portion of the annular surgical stapling device of FIG. 1, illustrating attachment points according to another embodiment of the present disclosure.
Figure 7C:
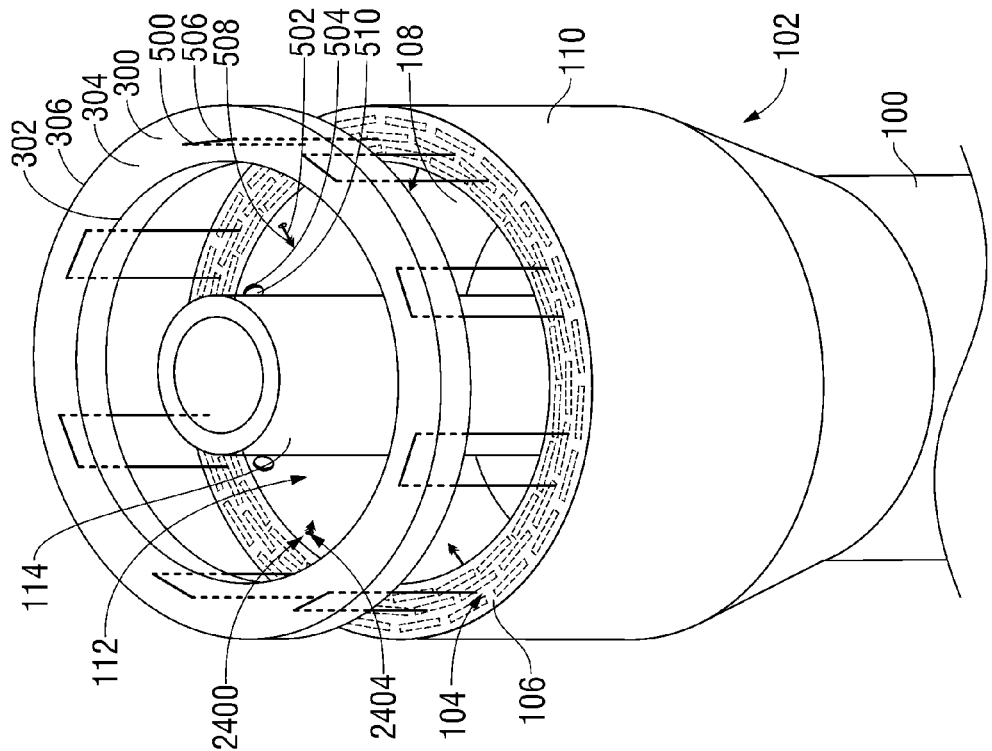
FIG. 7C is a perspective view, with parts separated, of the tubular body portion of FIG. 7A.
Figure 7B:
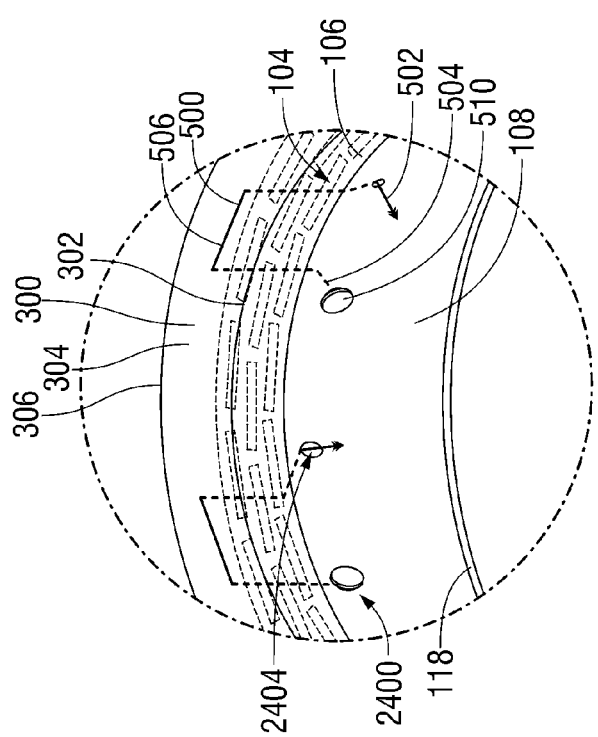
FIG. 7B is a detail view of a portion of the tubular body portion of FIG. 7A, illustrating the attachment points.

In another embodiment, as illustrated in FIGS. 7A-7C, attachment points 2400 are openings 2404 extending through inner surface 108 of staple cartridge assembly 102. In this embodiment, leading end 502 of suture 500 includes a barbed tip 508 such as, for example a unidirectional barb, single barb, composite barb or other suitable barb, and trailing end 504 of suture 500 includes a stop member 510. Barbed tip 508 may also extend along at least a portion of body portion 506. Stop member 510 may include a button, knob, or other similar element which is suitable for preventing or limiting advancement of trailing end 504 through openings 2404. Stop member 510 may also or alternatively be formed by heat mushrooming at trailing end 504 and may have a transverse dimension that is greater than a transverse dimension of openings 2404. Initially leading end 502 is inserted through a first of openings 2404 through the tissue contacting surface 106 of staple cartridge assembly 102 and through a first portion of the buttress material 300 until stop member 510 engages the first of openings 2404 to limit further advancement of suture 500 through the first opening 2404. Leading end 502 is then inserted through a second portion of the buttress material 300, through tissue contacting surface 106, and through a second of openings 2404 until body portion 506 engages buttress material 300 to secure buttress material 300 to tissue contacting surface 106 of staple cartridge assembly 102. Suture 500 may also extend through one or more of staple receiving slots 104.

In an embodiment, it is contemplated that openings 2404 may include a silicon or gel like material for engaging barbed tip 508 to limit withdrawal of suture 500 from openings 2404. Openings 2404 may also or alternatively extend through outer surface 110 of staple cartridge assembly 102.

As described above, sutures 500 are configured to break free or be severed from staple cartridge assembly 102 upon firing of the annular surgical stapling device 10. The suture 500 may also be configured to be cut or severed by the knife 118 as the knife 118 is actuated to sever tissue "T" where, for example, one or both of barbed tip 508 and stop member 510 may be severed by the knife 118 during firing of surgical stapling device 10. The surgeon may also manipulate the suture 500 to release suture 500 from staple cartridge assembly 102 during or after firing of annular surgical stapling device 10.

Figure 8:
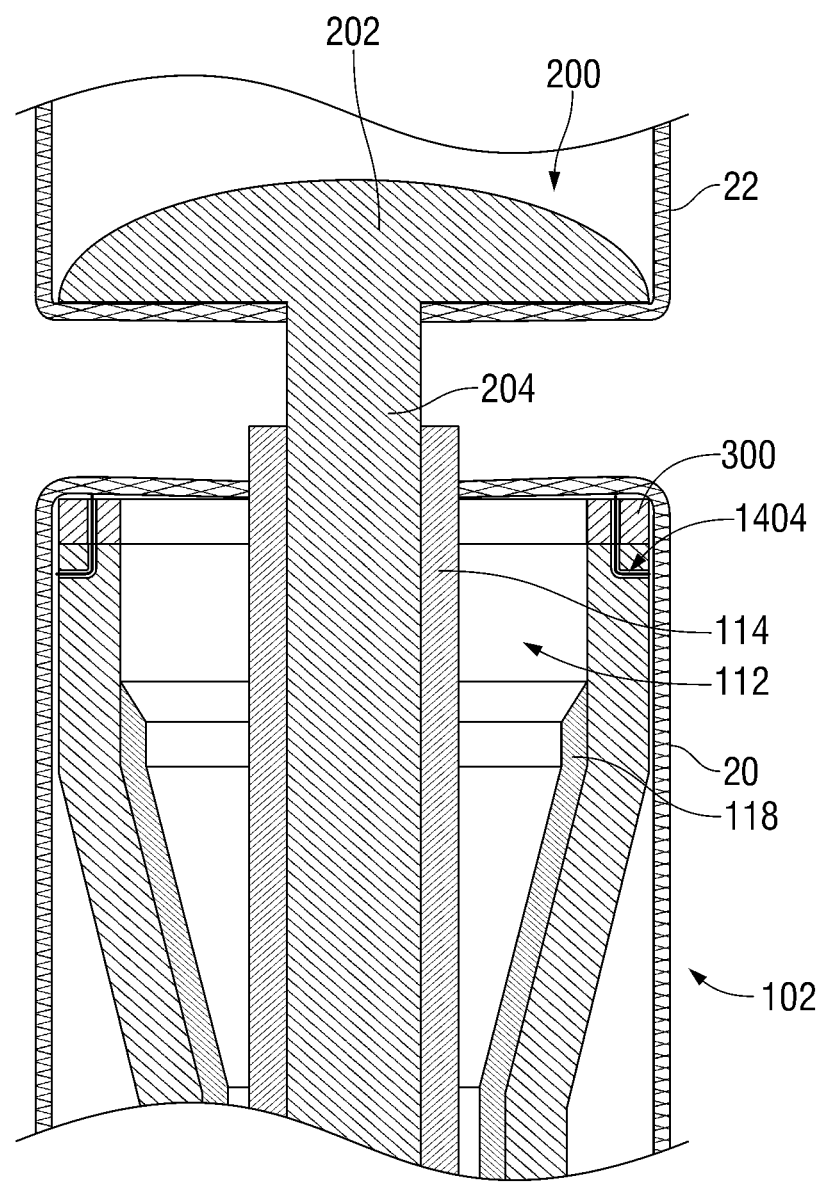
FIG. 8 is a schematic, longitudinal, cross-sectional view of the annular surgical stapling device of FIG. 4A, illustrating the buttress material of FIG. 2 secured to the staple cartridge assembly of the tubular body portion with tissue disposed between the buttress material and the anvil assembly of the annular surgical stapling device.
Figure 9:
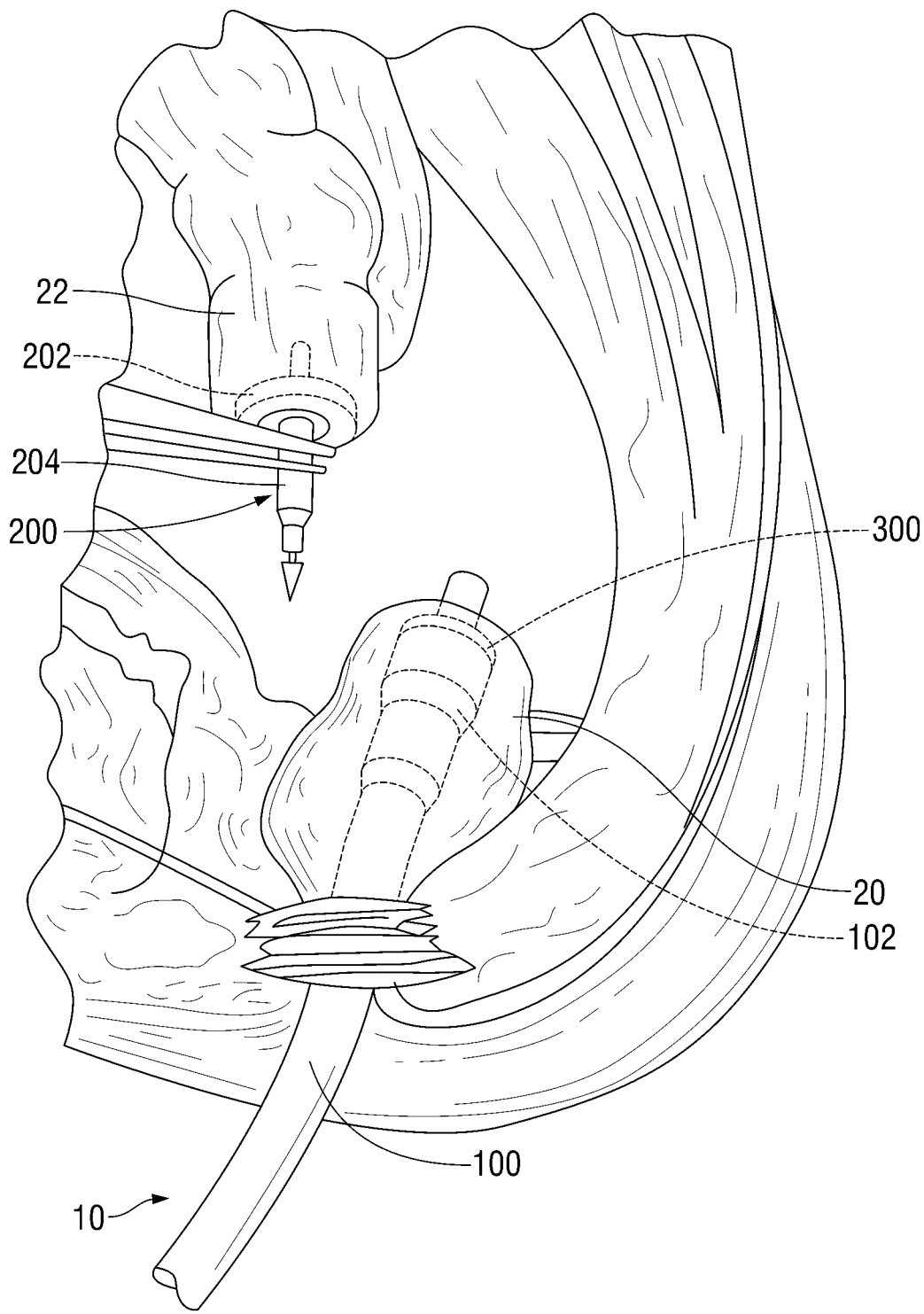
FIG. 9 is a perspective view of the intestinal area of a patient, illustrating a method of positioning the annular surgical stapling device of FIG. 1 to connect the anvil assembly to the tubular body portion.

Turning now to FIGS. 8 and 9, there is illustrated the use of annular surgical stapling device 10 and detachable anvil assembly 200 in an anastomosis procedure to effect joining of intestinal sections 20 and 22. The anastomosis procedure is typically performed using minimally invasive surgical techniques including laparoscopic means and instrumentation. At the point in the procedure shown in FIG. 9, a diseased intestinal section has been previously removed, anvil assembly 200 has been applied to the operative site either through a surgical incision or transanally and positioned within intestinal section 22, and tubular body portion 100 of annular surgical stapling device 10 has been inserted transanally into intestinal section 20. Intestinal sections 20 and 22 are also shown temporarily secured about their respective components (e.g., shaft 204 of anvil assembly 200, and the central shaft 114 of tubular body portion 100 by a purse-string suture or the like).

According to one method, with reference to FIGS. 4A-4C, 5A-5D, 6A-6C, 7A-7C, and as seen in FIGS. 8 and 9, buttress material 300 may be positioned and secured to the tissue contacting surface 106 of tubular body portion 100 by sutures 500 prior to the coupling of anvil assembly 200 to the central shaft 114 of tubular body portion 100. Tubular body portion 100 may come with buttress material 300 pre-positioned and secured to tissue contacting surface 106 by sutures 500. Alternatively the surgeon may secure buttress material 300 to tissue contacting surface 106 prior to use. With buttress material 300 secured in place, the surgeon maneuvers anvil assembly 200 until the proximal end of shaft 204 is inserted into the central shaft 114 of tubular body portion 100. Central shaft 114 is now engaged to shaft 204 with intestinal sections 20 and 22 disposed between anvil assembly 200 and staple cartridge assembly 102. As seen in FIG. 9, for example, buttress material 300 is disposed between cartridge assembly 102 and intestinal sections 20 and 22.

Anvil assembly 200 and tubular body portion 100 are then approximated to approximate intestinal sections 20, 22 and capture buttress material 300 between intestinal section 20 and tissue contacting surface 106 of staple cartridge assembly 102. Surgical stapling device 10 is then fired to staple buttress material 300 and intestinal sections 20, 22 together and the knife 118 is actuated to cut the portion of tissue and any portion of buttress material 300 and any portion of suture 500 disposed radially inward of knife 118 or extending across knife 118, to complete the anastomosis. The staples 116 which are driven or fired through staple receiving slots 104 may sever or break any portion of suture 500 disposed or extending through staple receiving slots 104 during the firing process. Once anastomosis is complete anvil assembly 200 and tubular body portion 100 are unapproximated to release intestinal sections 20, 22 and buttress material 300. Sutures 500 may break or sever upon release of intestinal sections 20, 22 or as described above, may be released by the surgeon or severed by the knife 118.

Figure 10:
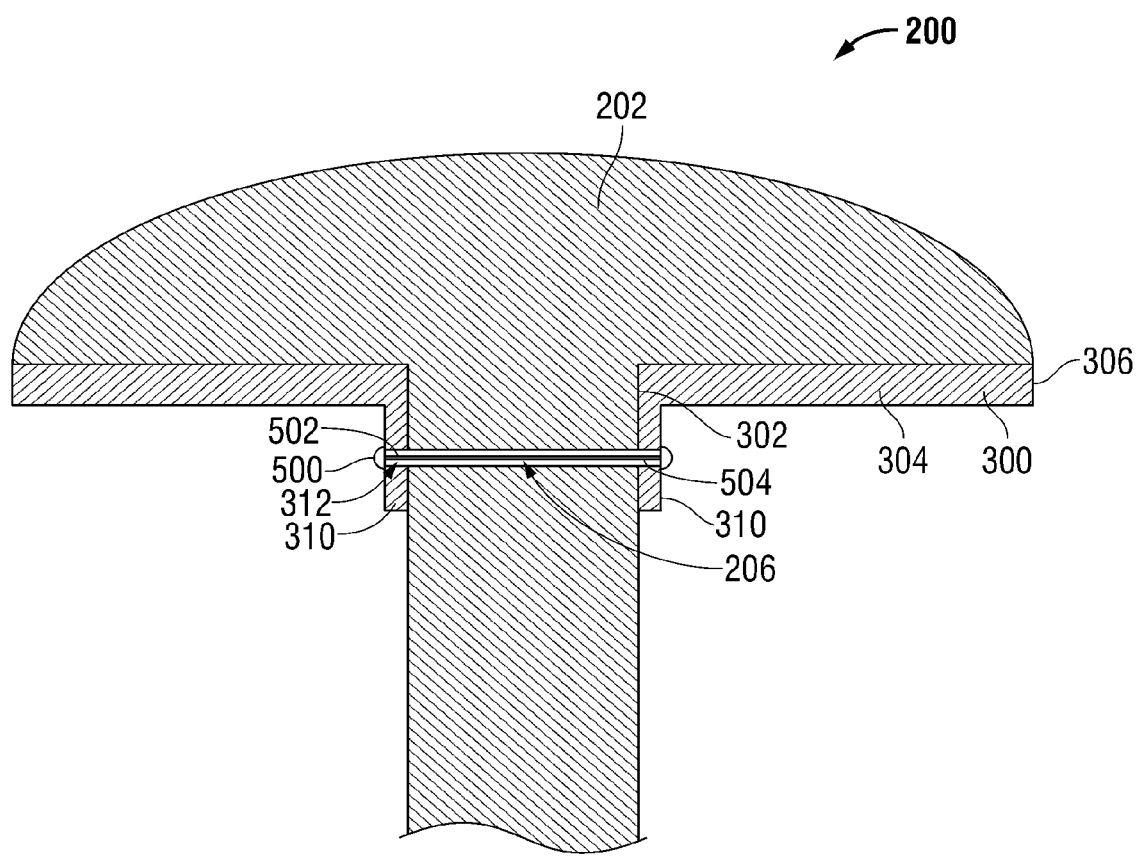
FIG. 10 is a schematic, longitudinal cross-sectional view of the anvil of the annular surgical stapling device of FIG. 1, illustrating the buttress material secured to the anvil by a suture extending through a lumen of the anvil.
Figure 11:
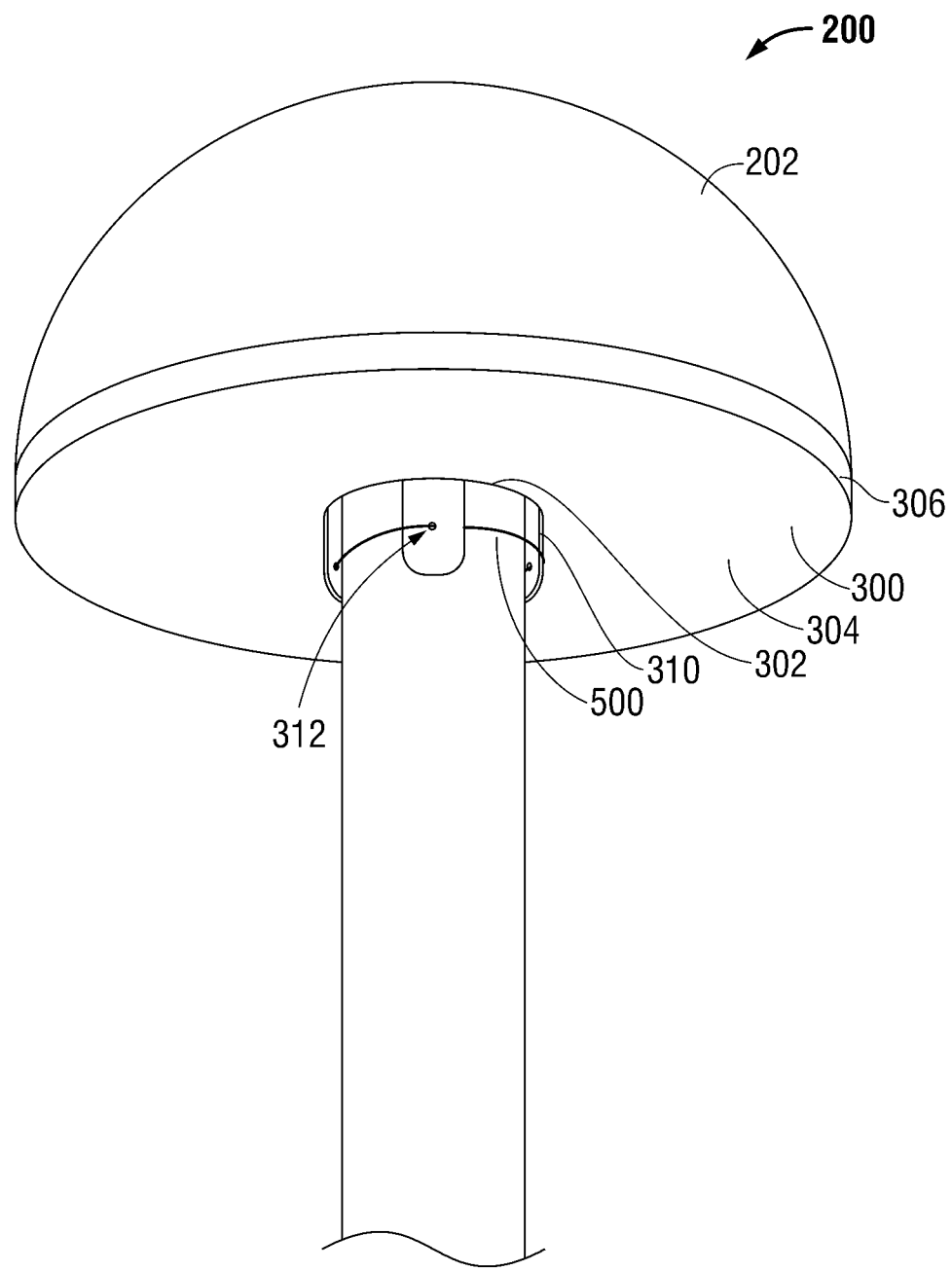
FIG. 11 is a perspective view of the anvil of the annular surgical stapling device of FIG. 1, illustrating the buttress material secured to the anvil by a suture inserted annularly through the buttress material circumferentially about the anvil.

In another embodiment, referring now to FIGS. 10 and 11, buttress material 300 may be secured to the anvil assembly 200 instead of staple cartridge assembly 102. In this embodiment, aperture 308 of buttress material 300 is dimensioned to receive shaft 204 of anvil assembly 200 such that inner portion 302 of buttress material 300 abuts or is proximate to shaft 204. Buttress material 300 further includes flanges or tabs 310 extending from inner portion 302 of buttress material 300 with flanges 310 extending axially from inner portion 302 of buttress material 300 along shaft 204.

As illustrated in FIG. 10, shaft 204 includes a lumen 206 extending therethrough between opposite flanges 310 of buttress material 300. Leading end 502 of suture 500 is inserted through a first of flanges 310, through lumen 206, and through a second of flanges 310 on an opposite side of shaft 204. Similar to the above embodiments, leading and trailing ends 502, 504 of suture 500 may include buttons, knobs, stop members, barbs or other similar mechanisms for limiting advancement or withdrawal of suture 500 through flanges 310 and lumen 206. Leading and trailing ends 502, 504 may also be heat mushroomed or sealed after insertion. Additional flanges 310 and/or lumens 206 may be included about the circumference of inner portion 302 of buttress material 300 and of shaft 204 respectively to further secure buttress material 300 to anvil assembly 200. Although illustrated as substantially linearly extending through shaft 204, lumens 206 may also or alternatively define arcuate or angled paths through shaft 204 where, for example, adjacent flanges 310 may be aligned with a single lumen 206 instead of opposite flanges 310. For example, lumens 206 may define a ninety degree angle through shaft 204 or may define a larger or smaller angle through shaft 204. Lumen 206 may also or alternatively define a curved or arcuate path through shaft 204. Leading end 502 of suture 500 may be inserted through flanges 310 by piercing flanges 310 or flanges 310 may, for example, include one or more holes 312 for receiving sutures 500 therethrough.

In another embodiment, as illustrated in FIG. 11, suture 500 may instead be threaded through flanges 310 to encircle or surround shaft 204 and form a purse string. For example, suture 500 may be annularly stitched through flanges 310 or buttress 300 about shaft 204 of anvil assembly 200. The annularly stitched suture 500 is transitionable between a first configuration defining a first diameter which is larger than the outer diameter of shaft 204 and a second configuration which is substantially the same as the outer diameter of shaft 204. As suture 500 is transitioned to the second configuration and tightened about shaft 204, flanges 310 press against shaft 204 to secure buttress material 300 in place against shaft 204. Buttress material 300 may be released from anvil assembly 200 in a manner similar to those described above in previous embodiments. Suture 500 may alternatively be annularly threaded or inserted through inner portion 302 of buttress material 300 instead of flanges 310.

In both of the above embodiments, buttress material 300 may be separated from anvil assembly as described above through breakage or slippage. For example, the surgeon may manipulate suture 500 to release buttress material 300 or suture 500 may be adapted or configured to break or sever after firing of surgical stapling device 10. Alternatively, during firing, actuation of knife 118 may sever the portion of buttress material 300 disposed radially inward of the inner surface 108 of staple cartridge assembly 102, and may sever suture 500, from the portion of buttress material 300 disposed on the staple cartridge assembly 102 such that only the anastomized portion of buttress material 300 remains attached to the intestinal sections 20, 22. In this way the remaining portion of buttress material 300 remains secured to the anvil assembly 200 for removal from the patient's body.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A method of using a buttress material with a surgical stapling device, the method comprising:
    positioning the buttress material at least partially between an anvil assembly and a cartridge assembly of the surgical stapling device;
    securing the buttress material to the surgical stapling device by engaging a suture with the buttress material and extending the suture through a tubular body portion of the cartridge assembly, the suture having a first end and a second end;
    receiving body tissue between the anvil assembly and the cartridge assembly;
    grasping the body tissue between the anvil assembly and the cartridge assembly;
    firing the surgical stapling device to drive a plurality of staples from the cartridge assembly through the buttress material and the body tissue; and
    releasing the suture from the surgical stapling device to release the buttress material from the surgical stapling device.

2. A method according to claim 1, wherein securing of the buttress material to the surgical stapling device includes inserting at least one of the first end of the suture or the second end of the suture through at least one hole of the tubular body portion of the cartridge assembly.

3. A method according to claim 1, wherein securing of the buttress material to the surgical stapling device includes inserting the first end of the suture through a first hole of the tubular body portion and inserting the second end of the suture through a second hole of the tubular body portion.

4. A method according to claim 3, wherein securing of the buttress material to the surgical stapling device includes:
    knotting the first end of the suture, thereby preventing the first end of the suture from passing through the first hole of the tubular body portion; and
    knotting the second end of the suture, thereby preventing the second end of the suture from passing through the second hole of the tubular body portion.

5. A method according to claim 3, wherein securing of the buttress material to the surgical stapling device includes a second suture having a first end and a second end, inserting the first end of the second suture through a third hole of the tubular body portion and inserting a second end of the second suture through a fourth hole of the tubular body portion, and knotting the second end of the first suture and the first end of the second suture together.

6. A method according to claim 3, wherein securing of the buttress material to the surgical stapling device includes:
    heat mushrooming the first end of the suture, thereby preventing the first end of the suture from passing through the first hole of the tubular body portion; and heat mushrooming the second end of the suture, thereby preventing the second end of the suture from passing through the second hole of the tubular body portion.

7. A method according to claim 3, wherein securing of the buttress material to the surgical stapling device includes:
attaching a stop member to the first end of the suture, thereby preventing the first end of the suture from passing through the first hole of the tubular body portion; and
attaching a stop member to the second end of the suture, thereby preventing the second end of the suture from passing through the second hole of the tubular body portion.

8. A method according to claim 1, wherein securing of the buttress material to the surgical stapling device includes inserting the second end of the suture through a first hole of the tubular body portion, through a tissue contacting surface of the tubular body portion and through a second hole of the tubular body portion.

9. A method according to claim 8, wherein the second end of the suture is a barb and the first end of the suture is a stop member.

10. A method according to claim 9, wherein the barb is a unidirectional barb, a single barb, or a composite barb.

11. A method according to claim 1, wherein securing of the buttress material to the surgical stapling device includes removably attaching the suture to an attachment portion of the surgical stapling device.

12. A method according to claim 11, wherein securing of the buttress material to the surgical stapling device includes inserting the first end of the suture and the second end of the suture through a cleat defined by the attachment portion of the surgical stapling device.

13. A method according to claim 1, wherein releasing of the suture includes severing the suture with a knife blade disposed in the tubular body portion and movable relative to the tubular body portion.

14. A method according to claim 13, wherein releasing of the suture includes releasing the suture from the attachment portion of the surgical stapling device.

15. A method according to claim 1, wherein securing of the buttress material to the surgical stapling device includes securing the buttress material at least partially to a distal end of the tubular body portion.

\* \* \* \* \*